(12) United States Patent
Kahn et al.

(10) Patent No.: US 11,382,534 B1
(45) Date of Patent: Jul. 12, 2022

(54) SLEEP DETECTION AND ANALYSIS SYSTEM

(71) Applicants: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US); Andrew Cotton-Clay, Santa Cruz, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US); Andrew Cotton-Clay, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 128 days.

(21) Appl. No.: 16/601,567

(22) Filed: Oct. 14, 2019

Related U.S. Application Data

(60) Provisional application No. 62/745,976, filed on Oct. 15, 2018, provisional application No. 62/745,984, (Continued)

(51) Int. Cl.
*A61B 5/11* (2006.01)
*A61B 5/00* (2006.01)
(Continued)

(52) U.S. Cl.
CPC .......... *A61B 5/1126* (2013.01); *A47C 27/083* (2013.01); *A61B 5/0205* (2013.01);
(Continued)

(58) Field of Classification Search
CPC ... A61B 5/4809; A61B 5/4812; A61B 5/1118; A61B 5/11; A61B 5/1115; A61B 5/6892;
(Continued)

(56) References Cited

U.S. PATENT DOCUMENTS 3,683,933 A 8/1972 Mansfield
6,014,682 A 1/2000 Stephen et al.
(Continued)

OTHER PUBLICATIONS

Internet Archive, Withings "Sleep Tracking Mat" Nov. 22, 2018. Retrieved from https://web.archive.org/web/20181122024547/https://www.withings.com/us/en/sleep (Year: 2018).*
(Continued)

*Primary Examiner* — David J. McCrosky
(74) *Attorney, Agent, or Firm* — Nicholson De Vos Webster & Elliott LLP; Judith Szepesi

(57) ABSTRACT

A method of detecting the presence of a person on a bed comprising, receiving movement data in pseudo-real-time, extracting features from the movement data for a time period in pseudo-real-time, determining whether the bed is occupied for the time period in pseudo-real-time, for each time period in which the bed is indicated as occupied, determining a user on a side of the bed, based on data from a plurality of time periods, and utilizing a sleep engine to determine sleep stages for the user. The method in one embodiment further comprising flagging when a majority of the plurality of time periods indicate that the sleep stage for the user is awake and providing a sleep recording to the user, showing the sleep stages for the user.

14 Claims, 15 Drawing Sheets

Related U.S. Application Data filed on Oct. 15, 2018, provisional application No. 62/745,978, filed on Oct. 15, 2018.

(51) Int. Cl.
*A47C 27/08* (2006.01)
*A61B 5/0205* (2006.01)

(52) U.S. Cl.
CPC .......... *A61B 5/1118* (2013.01); *A61B 5/4809* (2013.01); *A61B 5/4812* (2013.01); *A61B 5/7264* (2013.01)

(58) Field of Classification Search
CPC .......... A61B 5/6891; A61B 2562/0219; A61B 5/4806; A61B 5/4815; A61B 5/4818; A61B 5/7264; A47C 27/083
See application file for complete search history.

(56) References Cited

U.S. PATENT DOCUMENTS

| | | |
|---|---|---|
| 7,139,342 B1 | 11/2006 | Phanse |
| 8,909,357 B2* | 12/2014 | Rawls-Meehan .... A47C 21/003 700/17 |
| 2004/0071382 A1 | 4/2004 | Rich et al. |
| 2007/0093722 A1* | 4/2007 | Noda .................. A61B 5/6892 600/533 |
| 2008/0269625 A1 | 10/2008 | Halperin et al. |
| 2010/0010565 A1 | 1/2010 | Lichtenstein et al. |
| 2011/0304240 A1 | 12/2011 | Meitav et al. |
| 2013/0197857 A1 | 8/2013 | Lu et al. |
| 2014/0350351 A1* | 11/2014 | Halperin .............. A61B 5/6892 600/300 |
| 2015/0094544 A1 | 4/2015 | Spolin et al. |
| 2015/0164409 A1* | 6/2015 | Benson .................. A61B 7/003 600/301 |
| 2015/0333950 A1 | 11/2015 | Johansson |
| 2016/0287869 A1 | 10/2016 | Errico et al. |
| 2017/0188938 A1* | 7/2017 | Toh ...................... A61B 5/0022 |
| 2018/0103770 A1* | 4/2018 | Nava .................. A47C 21/026 |
| 2019/0044380 A1 | 2/2019 | Lausch et al. |
| 2019/0132570 A1 | 5/2019 | Chen et al. |

OTHER PUBLICATIONS

Crist, CNET "Samsung introduces SleepSense" Sep. 3, 2015. Retrieved from https://www.cnet.com/reviews/samsung-sleepsense-preview (Year: 2015).*

Campbell, Appleinsider, "Apple buys sleep tracking firm Beddit" May 9, 2017. Retrieved from https://appleinsider.com/articles/17/05/09/apple-buys-sleep-tracking-firm-beddit (Year: 2017).*

* cited by examiner

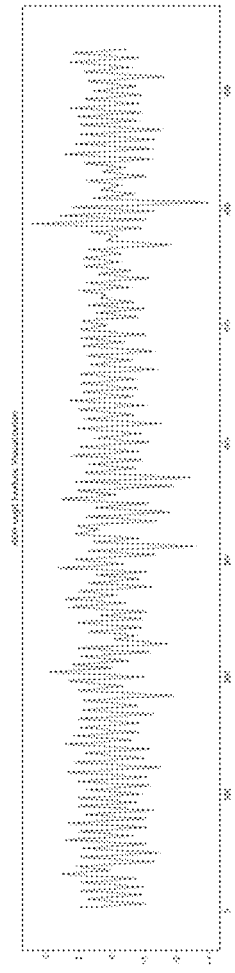
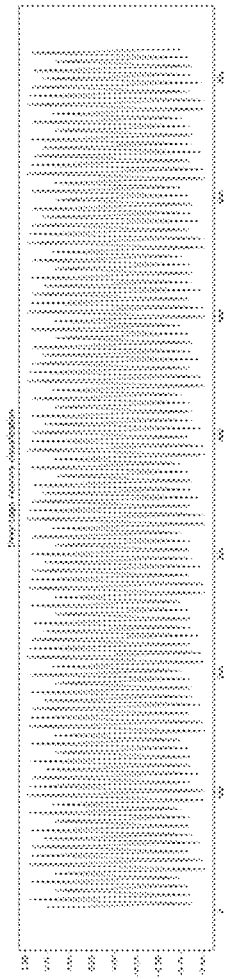
Fig. 9B

SLEEP DETECTION AND ANALYSIS SYSTEM

RELATED APPLICATION

The present application claims priority to U.S. Provisional Patent Application 62/745,984 filed on Oct. 15, 2018. The present application also claims priority to U.S. Provisional Patent Application No. 62/745,978 (8689P232Z) and U.S. Provisional Application No. 62/745,976 (8689P231Z) both filed on Oct. 15, 2019 and incorporates all three of those applications by reference in their entirety.

FIELD

The present invention relates to sleep sensors, and more particularly to an improved sleep detection system.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

Therefore, it is useful for everyone to know more about how well they sleep.

BRIEF DESCRIPTION OF THE FIGURES

The present invention is illustrated by way of example, and not by way of limitation, in the figures of the accompanying drawings and in which like reference numerals refer to similar elements and in which:

FIG. 9B illustrates the breathing patterns of two sleep stages.

DETAILED DESCRIPTION

Sleep analysis based on sensor data requires high accuracy. The present application uses artificial intelligence (AI) and complex analytics to identify when there is a sleeper in the bed, identify which sleeper it is in a shared bed, and associate the detected sleeping, breathing, heart rate, and snoring data to the appropriate user. In one embodiment, the system uses sensor fusion to join data from multiple sensors to reinforce the deductive systems. In one embodiment, the enhanced system is as accurate as polysomnographic analysis by experts. The detection system in one embodiment uses as its baseline force transmitted through a mattress from body movement due to breathing, heartbeat, micromovements, and larger scale movements. This piezo force sensor data is processed to capture all of the data, and to identify the portions of the data representing sleep state, respiration, heartbeat, and snoring, in one embodiment. Deep learning models use the data to calculate the sleep staging, e.g. determine the sleep phases for the user.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1:
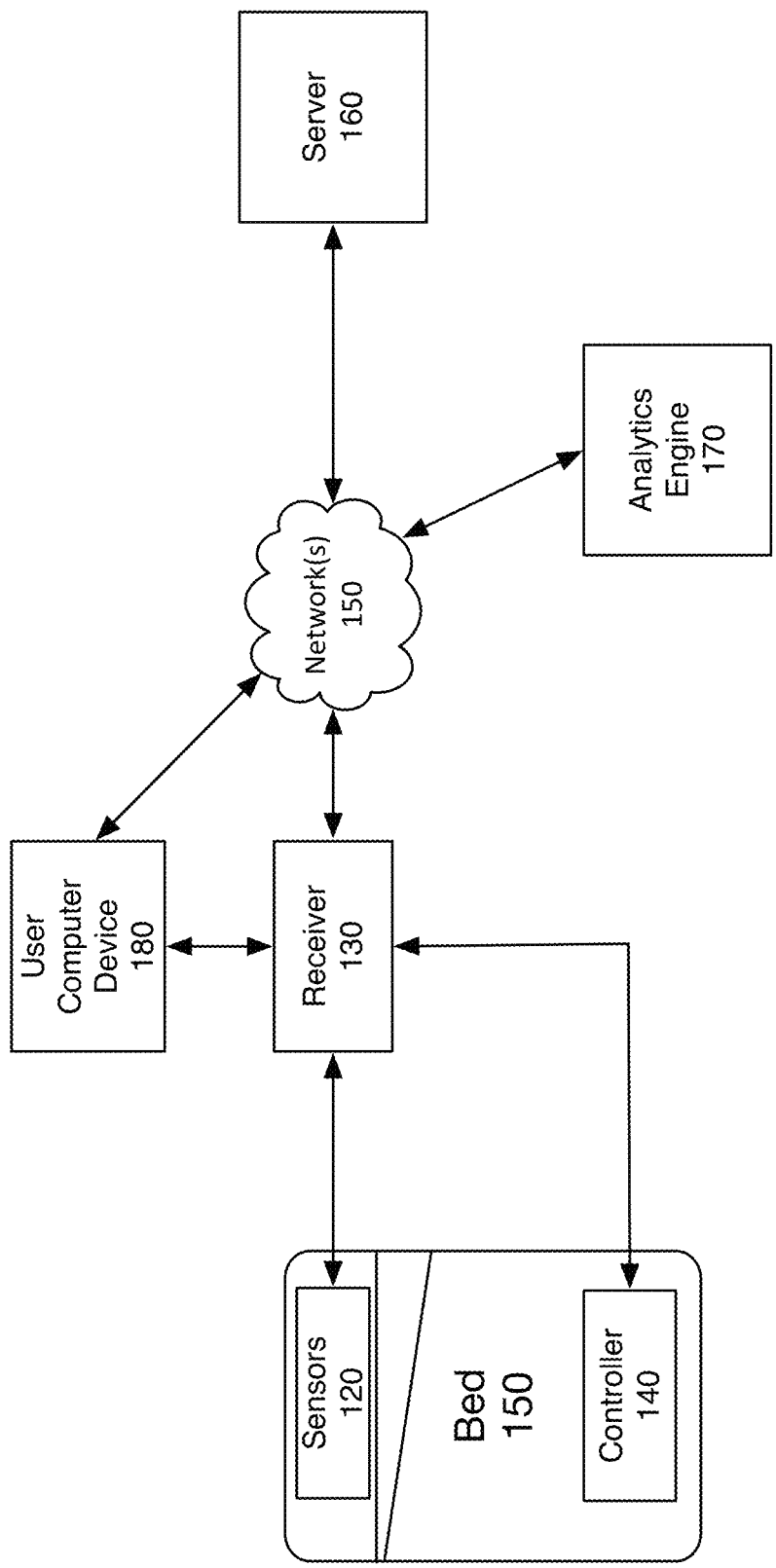
FIG. 1 is a block diagram of one embodiment of a system in which the present invention may be implemented.

FIG. 1 is block diagram of one embodiment of a system in which the sensor system may be implemented. The system includes a sleep analytics system 100 including sensors 120, receiver 130, server 160, and analytics engine 170. In one embodiment, the client portion of the sleep analytics system 100 is located in a user's home and includes the sensors 120 and receiver 130.

In one embodiment, the receiver 130 is coupled to sensors 120 via a cable. In another embodiment the connection may be wireless, such as low power Bluetooth (BLE), Wi-Fi, or another type of wireless connection. In one embodiment, receiver 130 also may be coupled to a controller 140, which controls bed 150. In one embodiment, this connection is a wired connection. Alternatively it may be a wireless connection. In one embodiment, the sensors 120 may include one or more sensors positioned in bed 150 which are used to measure the user's sleep. In one embodiment, sensors 120 may include sensors which are not in bed 150 but positioned in the room in which the bed 150 is located. In one embodiment, one or more these additional sensors may be built into receiver 130. In one embodiment, there may be external sensors which may be coupled to receiver 130 either via wires or wirelessly. The receiver 130 collects data from the one or more sensors, for transmission to the server 160.

In one embodiment, the receiver 130 is coupled to the server 160 via a network 150. The server portion includes server 160 and analytics engine 170, which in one embodiment are located off-site, removed from the user. In another embodiment, the server may be a local system, such as a computer system running an application. The network 150 may be the Internet, and the receiver 130 may send data to the server via a wireless network, such as Wi-Fi or the cellular network. In one embodiment, server 160 and analytics engine 170 may be on the same physical device. In one embodiment, server and/or analytics engine 170 may include a plurality of devices. In one embodiment, one or both of the server 170 and the analytics engine 170 may be using cloud computing and may be implemented as a distributed system.

In one embodiment, the user may be provided information about their sleep experience and the ability to set preferences via a computer device 180. In one embodiment, the user computer device 180 may be a mobile telephone, tablet, laptop, or desktop computer running an application or providing access to a website. In one embodiment, the user computer device 180 may be an IoT device such as AMAZON's Alexa or GOOGLE Home, or APPLE Siri. In one embodiment, the user computer device 180 may obtain data from the server 160 and/or analytics engine 170 via the network 150. In one embodiment, the user computer device 180 may connect to the server 160/analytics engine 170 via the receiver 130.

Figure 2:
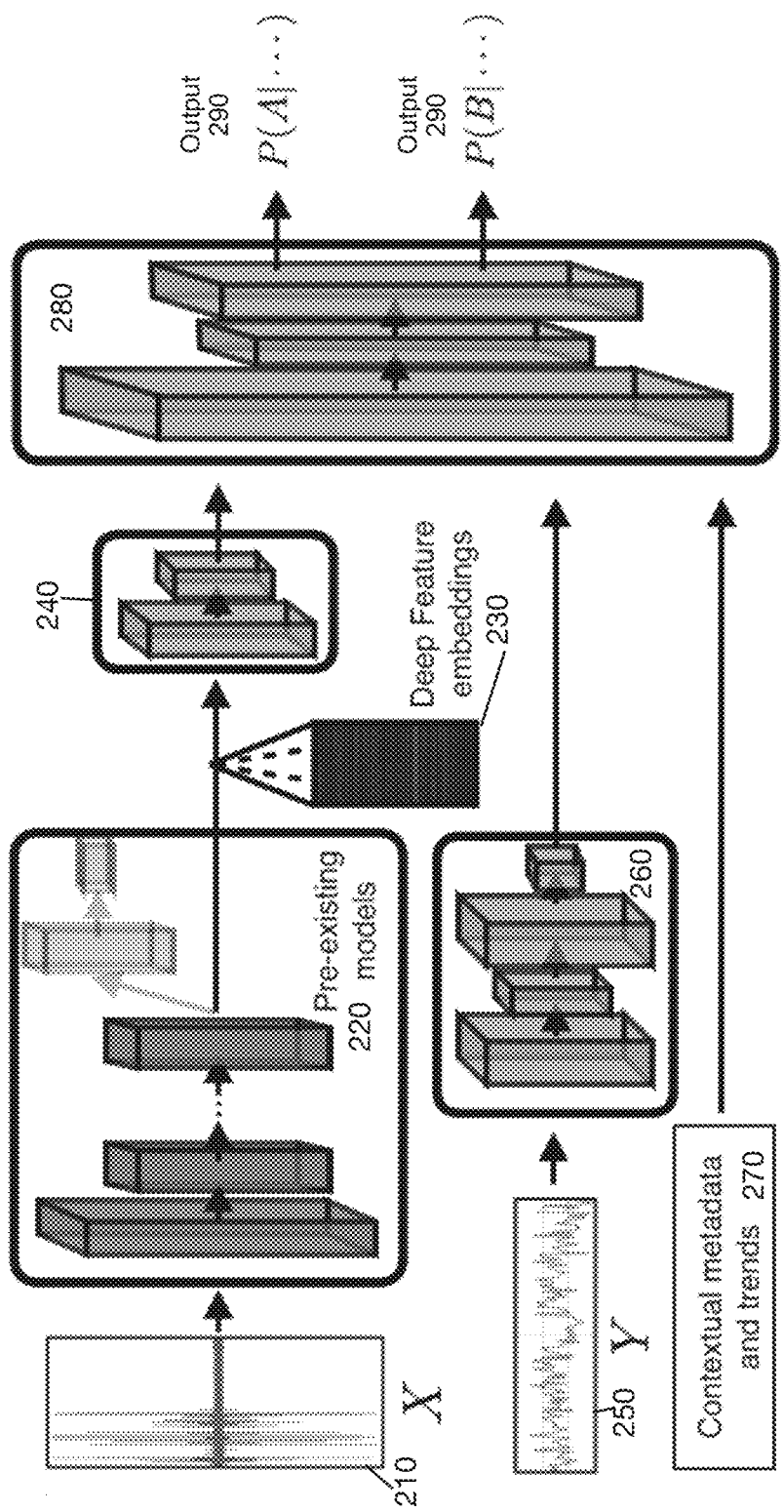
FIG. 2 is a block diagram of one embodiment of a model architecture that may be used with the present invention.

FIG. 2 is a block diagram of one embodiment of a model architecture that may be used with the present invention. In one embodiment, in an environment where in addition to the force sensor in the mattress, there may be other sensors available, for example a phone, watch, third party-in-home device, the data from those additional devices may be added. This sensor fusion of data in one embodiment uses audio data from a microphone, accelerometer data, and gyroscopic data in addition to the force sensing data. In one embodiment, the accelerometer and gyroscope may be on a body-worn device such as a smart watch or wristband. Additionally, in one embodiment, other sensors such as a CO2 sensor, or a volatile organic compound (VOC) sensor may also be added to the analysis.

Movements include voluntary or involuntary motions and movements that the user is not aware of such as body movements synchronized with the periodic mechanical pumping of the heart [or snoring or respiratory effort vibrating the body]. Movements can also manifest as audio sounds—such as the rustling sound from movement of bed sheets and comforters.

FIG. 2 illustrates one embodiment of how disparate "movement" information from an Audio sensor, X and an acceleration/force/pressure sensor Y may be integrated along with contextual information (such as the user's sleep schedule) to generate decisions. In one embodiment, as shown in the diagram, multi-layered neural networks are used on each sensor's data to generate intermediate features or embeddings. These are then further integrated by higher level layers to realize the final decision (for example, is the person Awake or Not).

In one embodiment, a deep learning VGG (visual geometry group) style classification model is used as an initial section. In one embodiment, this classification is used as the front end processing in an audio-sleep model. The multiple sensor streams are combined, as well as multiple signals per sensor stream (e.g. sub-bands) to improve accuracy.

The model architecture, in one embodiment, uses a sensor-fusion deep-learning architecture, for fast model development. In one embodiment, existing models are leveraged to extract deep features from raw data. The components and methods are reusable. In one embodiment, the preexisting model receive data, and are fused with the VGG type classification model, contextual metadata, and analytics of other sensor data streams (Y) to create a model architecture that can be used for sleep analytics.

Figure 3:
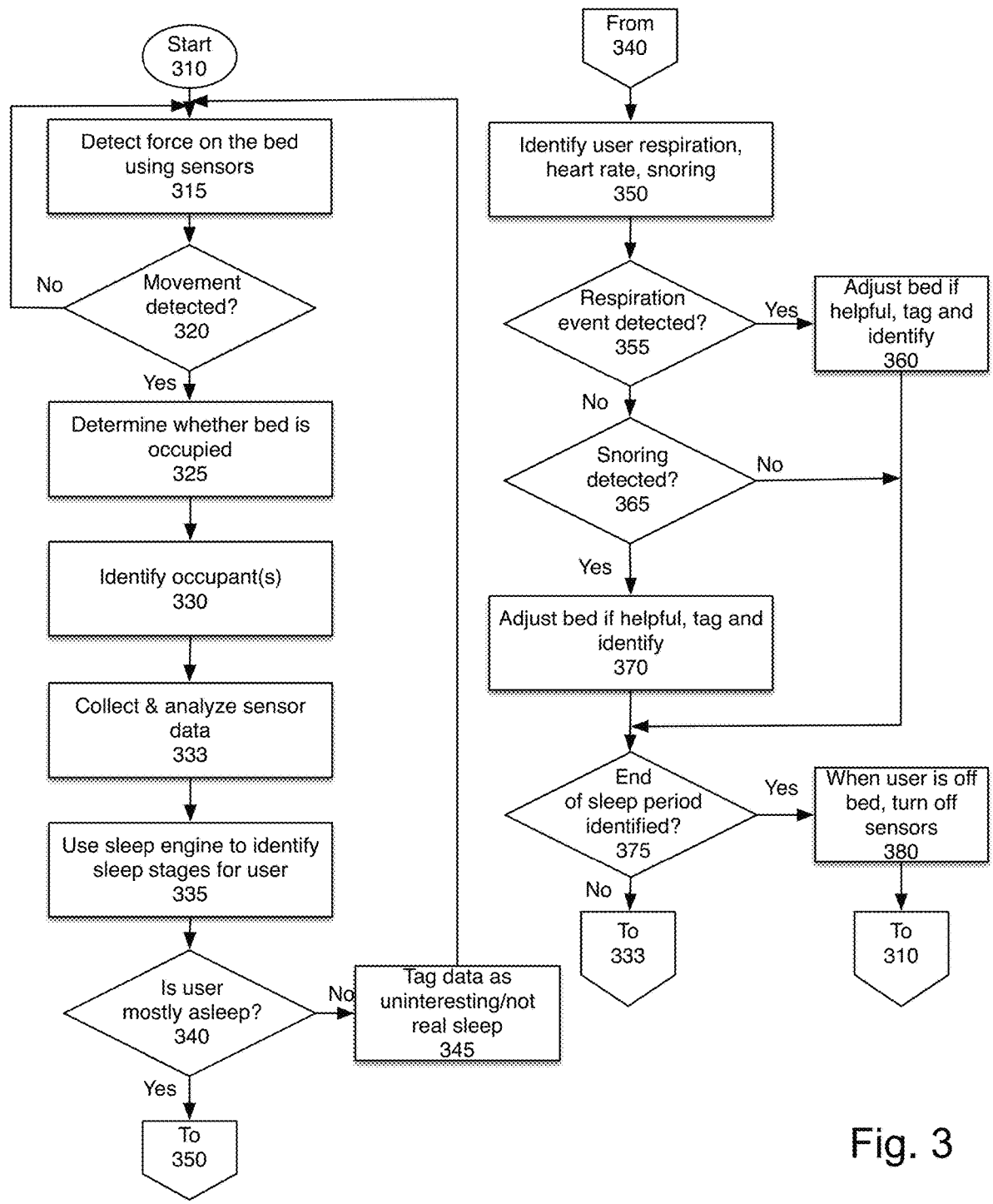
FIG. 3 is an overview flowchart of one embodiment of using the sleep analysis system.

FIG. 3 is an overview flowchart of one embodiment of using the sleep analysis system. The process starts at block 310. In one embodiment, this process is continuously available. In one embodiment, the process puts portions of the system to sleep if the system is inactive. For example, if there is no motion or force detected, or only motion/force below a threshold, the receiver may not transmit data to the server for analysis.

At block 315, the process detects force on the bed. At block 320, the process determines whether motion/force was detected. In one embodiment, a motion is indicated when a force above a threshold is detected. Because the piezoelectric sensors are extremely sensitive even a fan turning on would be detected as a force on the bed. However such force would not be considered movement, in one embodiment. In one embodiment, the force sensing threshold is set so the system does not turn on for air movements, placing a small object on the bed, or other such impacts on the bed. no movement is detected, the process continues to monitor at block 315.

If movement is detected, at block 325, the process determines whether the bed is occupied. This determination eliminates data from incidental movements, pets, or the placement of stationary objects on the bed. In one embodiment, occupation is determined based on tracking the micro-movements of the bed and mapping it to human micro-movements.

At block 330, the process identifies the occupant. In one embodiment, the occupant is identified only as "occupant on the right side" v. "occupant on the left side" of the bed. In another embodiment, the occupant is identified as one of the monitored individuals when possible. In one embodiment, this identification may occur after significant volume of data is collected. For example, the weight, breathing, and heart rate patterns of an individual are characteristic. Therefore, such data may be used to identify an individual.

At block 333, the system collects and analyzes sensor data. This is done continuously when the bed is occupied, in one embodiment. In one embodiment, in addition to real-time analysis there is retrospective analysis, as will be discussed in more detail below.

At block 335, a sleep engine is used to identify the sleep stages of the user. In one embodiment, this is done after data is collected, using real-time analytics as well as retrospective analytics, as will be described in more detail below.

At block 340, the process determines whether the user is mostly asleep during the period of the sleep being evaluated. In one embodiment, this is a determination based on the sleep stages analysis. In one embodiment, a user is mostly asleep if there is at least one sleep episode. In one embodiment, the user may need to be asleep for a minimum duration, such as 2-15 minutes, for it to be considered a sleep episode. In one embodiment, the user is mostly asleep when at least 50% of the time in bed is sleeping. If the user was not mostly asleep in one embodiment the data is tagged as uninteresting at block 345. In one embodiment, this data is also made available to the user but not indicated as sleep. This may be useful to the user to know that they did not fall asleep despite resting at a certain time. The process then returns to block 315 to continue monitoring the system and determine whether there is force detected by the sensors.

At block 350, the user's respiration and heart rate are detected. Because in one embodiment these detections are based on the same force data, in one embodiment, fused with some additional data, the system analyzes the combined data to identify the components. These aspects are not additive, and thus it is not possible to simply extract one aspect of the data. Rather the combined data must be analyzed to identify the individual events which indicate various events including respiration, heartbeat, and snoring. This is discussed in more detail below.

At block 355 the process determines whether a respiration event was detected. A respiration event may include incidents of apnea, as will be described below. If respiration events occur, at block 360 the system tags these events for the user's attention. In one embodiment, the system may alert the user to address their apnea, if it is above a threshold. In one embodiment, the bed may be automatically adjusted to address such respiration events, in real-time. For example, some sleepers have apnea issues when sleeping on their backs. Thus using the positioning or massaging elements in a bed to trigger the user to move from back sleeping to side sleeping may be utilized, in one embodiment.

Similarly, if snoring is detected at block 365 the bed may be adjusted at block 370. In one embodiment, the user may also be alerted. Further details on snoring detection are discussed below.

At block 375 the process determines whether the sleep period has ended. If not, the process returns to block 333 to continue to collect and analyze sensor data. If the sleep period has ended, and the user has left the bed, in one embodiment, some of the sensors are turned off, to reduce power consumption. The process then returns to block 315 to monitor for the next sleep episode.

Although FIG. 3 is illustrated as a flowchart one of skill in the art would understand that the process may be implemented as an interrupt driven system, in which detection and analysis is continuously updated as additional data is received. When certain characteristics are identified, such as a respiratory event or snoring, that data is tagged, and optionally addressed. Generally, unless the blocks depend on each other, the ordering of the process is arbitrary and may be altered without departing from the scope of the present application.

Figure 4:
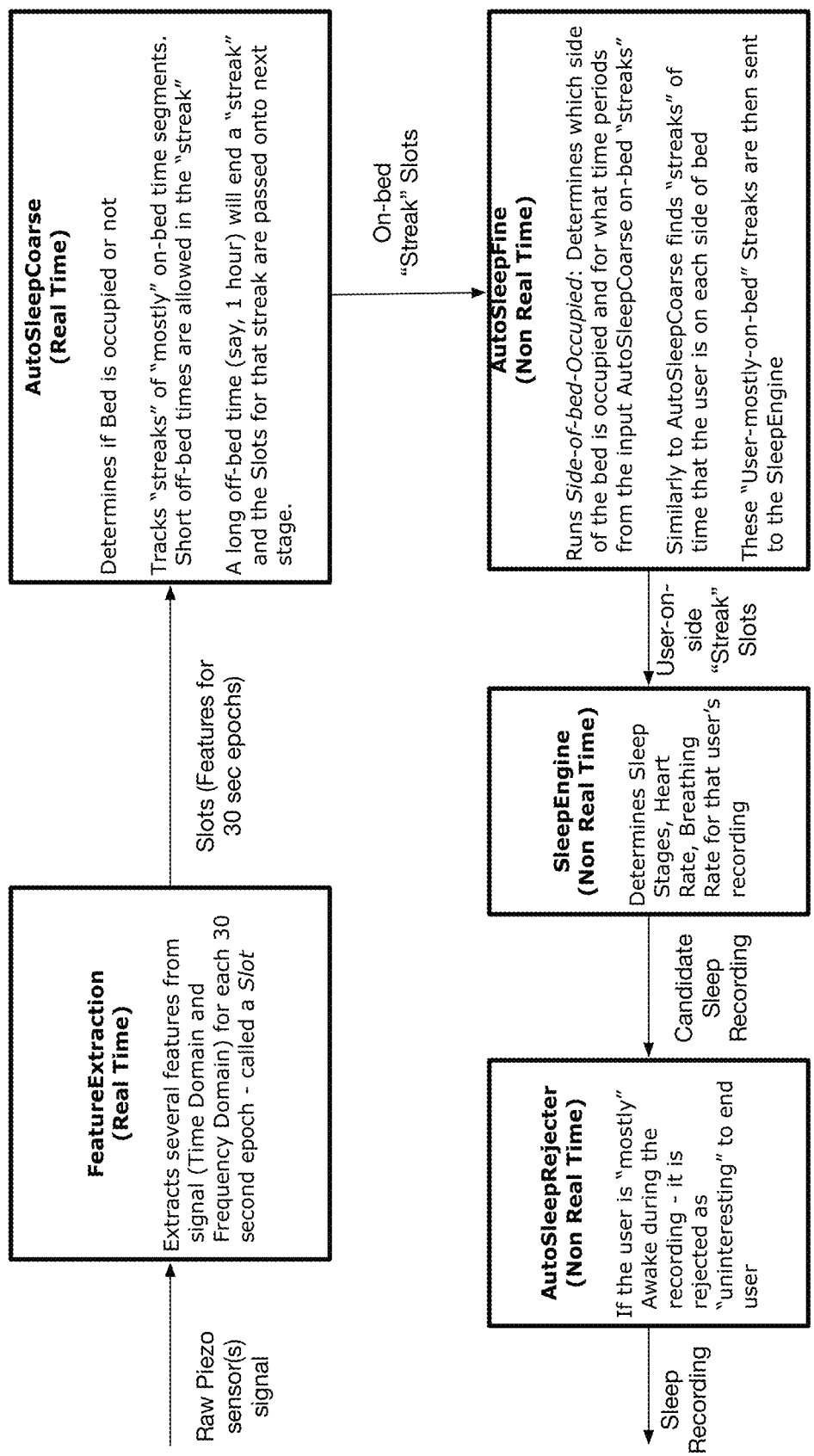
FIG. 4 is a flowchart of one embodiment of auto-sleep detection.

FIG. 4 is a flowchart of one embodiment of auto-sleep detection. An Automatic-Sleep-Recording system generates sleep recordings for the end user automatically without their intervention. In one embodiment, an optional "AutoSleep Stop" option allows the end user to get their recordings right after they get off the bed and not have to wait for the latency of AutoSleep.

Autosleep is Multi-Stage process in one embodiment. In one embodiment the process uses "Bed-Occupied" to find "extended" periods (or "streaks") of on bed for some-body on bed. Isolated and small (and likely misclassified sections) are not used, one embodiment.

The process uses "Side-of-Bed-Occupied" to find "extended" periods of time on the bed for a single user.

In one embodiment, the process uses Meta Information such as Sleep-Schedule (user specified schedule) to prune "uninteresting" sections.

In one embodiment, the system can learn users sleep schedule (vs blindly following user specified schedule). Frequently user specified schedules are "aspirational"—i.e. the user would like to sleep per that schedule but their real sleep schedule could be offset from their "aspirational").

The users on-bed and off-bed segments are recorded and fed into a clustering method to determine their true sleep schedule and also to automatically differentiate between weekday vs weekend schedules.

In one embodiment, the system may allow users to stop their sleep recording (and get a summary of) their recording sooner than having to wait for their partner to get off the bed as well. In one embodiment, the user may obtain their recording without stopping the recording.

In one embodiment, the system may allow users to end their recording when they get off bed and not wait for the retrospective processing to complete, which can take time. In one embodiment, the user may be provided an initial evaluation immediately, which may be updated after the retrospective processing is completed.

In one embodiment, the system may allow bed ridden users to get sleep recordings "chopped" at some daily boundary. Otherwise these users would never get any recording or if they eventually were not bed ridden the system would have a huge processing load for say several days of data to process for that user when they eventually stay off the bed for 1 hour.

In one embodiment, the AutoSleepCoarse real time process will periodically run AutoSleepFine's non-real-time processing blocks. If a user has a long-enough streak of on-the-side-of-bed, then their data will be sent to the SleepEngine to conclude their recording. In one embodiment, the period may be 1 hour.

In one embodiment, when a user is detected on the side of the bed (from above) an internal "AutoSleepPending" flag is set for that user and their Smartphone client will show a "recording-in-progress" screen that can be stopped by the end user via a stop button.

In one embodiment, when a user's (autosleep) recording exceeds a threshold time (as determined during the periodic checks described above)—the recording is automatically concluded at that point. In one embodiment, a user specified sleep schedule (say, 10 PM to 6 AM) is used to determine the cut-off (chop) point. In one embodiment, a chop point in the middle of the period outside of sleep schedule (for a sleep schedule of 10 PM to 6 AM this would be between 6 AM and 10 PM: i.e. 2 PM) is favored so as to return back more pleasing sleep recordings to the end user. An arbitrary chop point in the middle of a sleep schedule could fragment a user's overnight sleep into two sections and that may cause.

Figure 5:
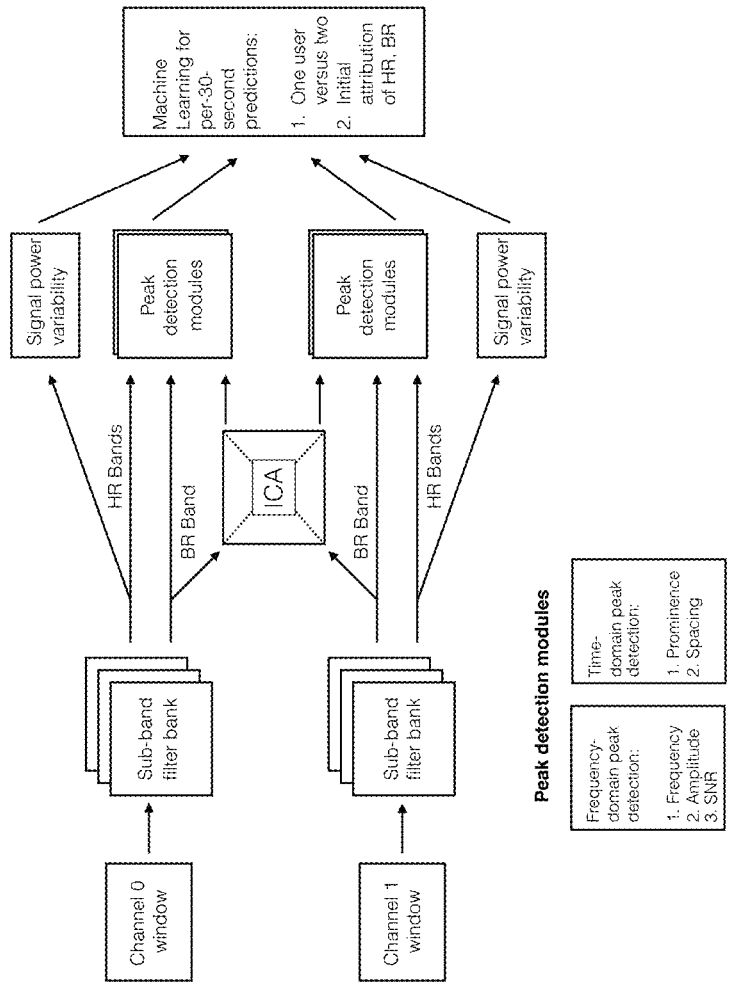
FIG. 5 is an analysis diagram of one embodiment of identifying the presence of one or more users in a bed.

FIG. 5 is an analysis diagram of one embodiment of identifying the presence of one or more users in a bed. In a standard bed, in one embodiment two piezo force sensors are placed underneath a mattress, at approximately head height, on both sides of the mattress. The system separates signals from these two sensors. In one embodiment, the sensor data for breathing rise and fall is separated based on frequency analysis and independent component analysis, and heart rate based on frequency analysis.

In one embodiment, the system uses frequency-domain data to detect signals in the piezo force sensors that resemble vital signs to classify every periodic data (in one embodiment 30 seconds) for the entire bed system as occupied or unoccupied. In one embodiment, the frequency-domain peak detection uses frequency, amplitude, and signal-to-noise ratio. In one embodiment, time-domain peak detection uses prominence and spacing of peaks for analysis.

In one embodiment, the system runs two interacting models: Longitudinal tracking of the characteristics of each bed system and clustering the signal, and strengths into low and high values for each individual bed system, and Deep learning on frequency-domain data to look for any sign of user presence, as distinguished from spurious mechanical or environmental activation of the piezo force sensors.

In one embodiment, for each segment of time, the system separates and provisionally attributes breathing rates, heart rates, and signal strength to each user. In one embodiment, a segment of time is 30 seconds. Alternatively, shorter or longer segments may be defined for this modeling.

Figure 6:
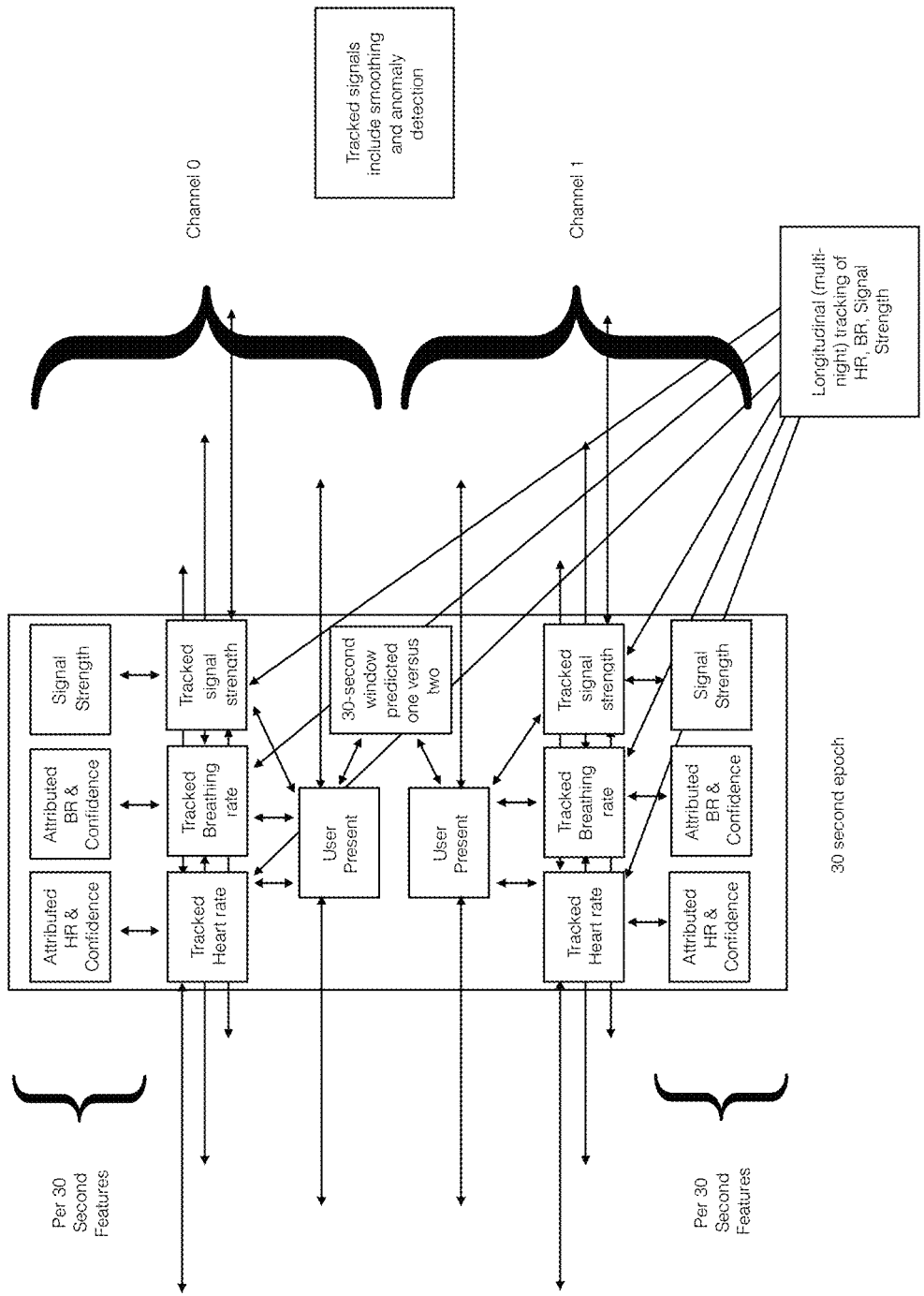
FIG. 6 is a block diagram of one embodiment of a system that may be used for identifying the presence of one or more users in the bed.

FIG. 6 is a block diagram of one embodiment of a system that may be used for identifying the presence of one or more users in the bed.

As noted above with respect to FIG. 5, the system tracks breathing rate, heart rate, and signal strength for likely transitions. By combining these transitions with the per-30-second multiple-users' prediction, the system makes a prediction for the full night based on a Bayesian Network model, in one embodiment. In one embodiment, the system additionally tracks statistics on breathing rate, heart rate, and signal strength longitudinally for each user, and uses this in the full night predictions.

In one embodiment, the full night predictions start with a provisional real-time prediction based on the inferences the system can draw from data prior to the given time. Then at the end of the night, the system updates these predictions with the inferences the system can draw from data later in the night. In one embodiment, this process starts from the end of the night and works backward. In one embodiment, the system has a tracked heart rate, breathing rate, and signal strength, attributed to the user, each of which has a confidence rating attached, evaluated per 30 second units. This data is used with a 30-second window of prediction of whether there are one or two sleepers on the bed, to output data for the sleepers on two channels. The cumulative data from the 30 second windows is used to generate the data. In one embodiment, some low confidence data may be removed. In one embodiment, unusual data requires a higher confidence level for display than expected data. For example, if the user's heart rate in one 30 second window is found to be 100 BPM, whereas the prior windows had the heart rate at 50 and 55 respectively, and the user does not have a history of such heart rate spikes, the system may consider that data incorrect, and discard it rather than displaying to the user. In one embodiment, the system includes anomaly detection, to remove erroneous data. Additionally, in one embodiment, smoothing may be applied to the tracked signals prior to evaluation.

Figure 7:
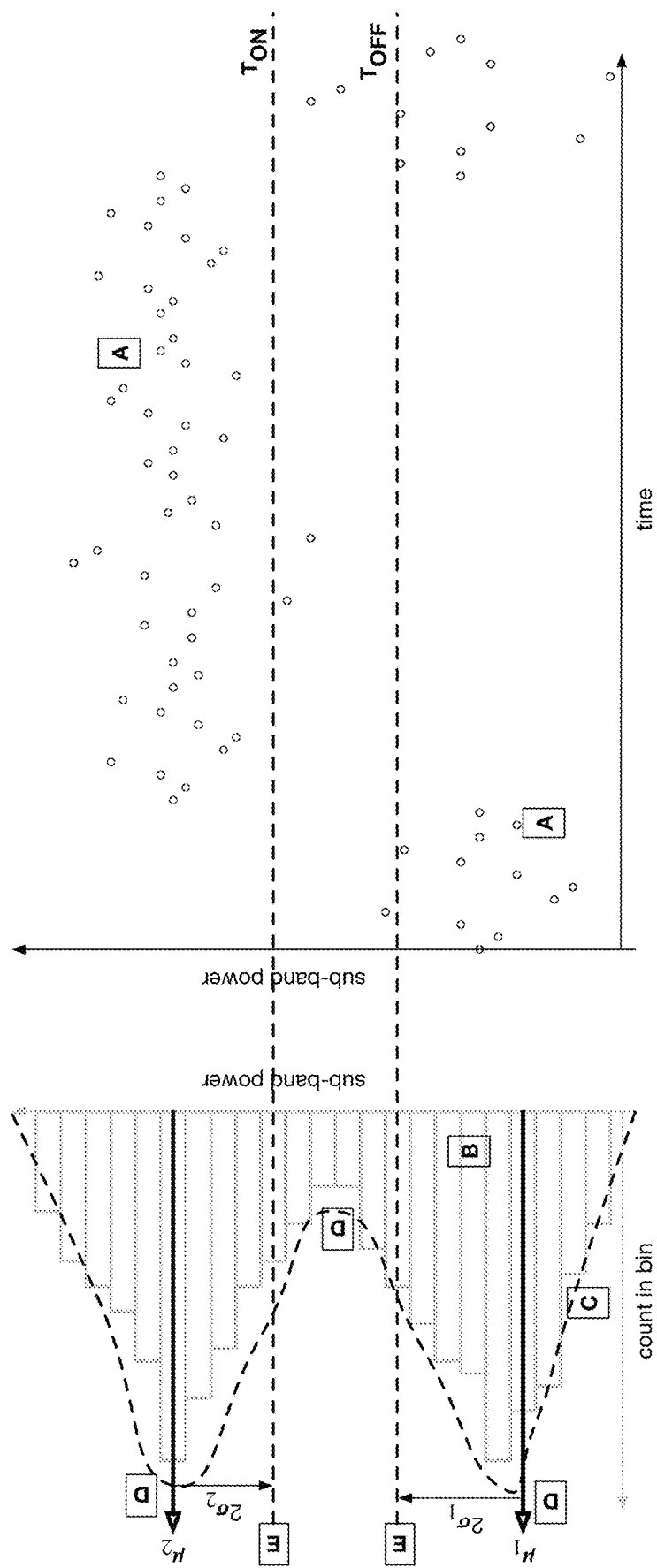
FIG. 7 is a diagram illustrating exemplary computing thresholds for identifying the presence of one or more users in the bed.

FIG. 7 is a diagram illustrating exemplary computing thresholds for identifying the presence of one or more users in the bed. FIG. 7 illustrates an unsupervised approach.

(A) A sub-band, named hrwbLF (Heart Rate Wide Band Low Frequency), is derived from the raw piezo signal with a band pass filter in the frequency range of 50 to 450 RPM. This frequency range includes the heart beat signal and its harmonics. Sub-band signal power, hrwbLFPower, is then computed over a look-back window size of 6.4 seconds and every 6 seconds. For each 30-second slot—the representational value is chosen as the minimum of its five values: p=min(log 10(hrwbLFPower))

(B) After initial setup of the sleep tracking system, these points, p, are collected for 18 hours and form distribution (B)

(C) The Kernel Density Estimation (KDE, https://en.wikipedia.org/wiki/Kernel_density_estimation) method is then used to derive a smoothed probability density estimate (C)

(D) The extrema (peaks and valleys) of this density estimate are then extracted. The peaks are characterized with their strength, spread, and relative prominence over surround (https://www.mathworks.com/help/signal/ref/findpeaks.html). Small peaks and those adjacent to large peaks and too close to it are removed. The peaks are then ordered lowest to highest along the 13-axis (sub-band power). The lowest and highest peaks are retained and their mean and standard deviation computed. These are $(\mu_1, \sigma_1), (\mu_2, \sigma_2)$ (E) Two thresholds $T_{OFF}$ and $T_{ON}$ are then chosen thus: $T_{OFF}$ is 2σ1 to the right of u1 and $T_{ON}$ is 2σ2 to the left of $\mu_2$ We validate that $T_{ON}$ and $T_{OFF}$ do not cross over and are a reasonable distance apart (i.e. that we keep $T_{ON} > T_{OFF}$+clearance)

Hysteresis Thresholding is used to determine final ON and OFF determination. In this approach—classification is done causally in time (i.e. with start at time 0 and proceeding to the 18 hour point in increments of time periods (in one embodiment 30 second slots) and determining a classification at each slot) with an initial seed value. If the classification currently is OFF then a value has to exceed $T_{ON}$ for the current classification to be changed to ON. Conversely if the current classification is ON the new signal value has to dip below $T_{OFF}$ for the classification to change to OFF. This "hysteresis" thresholding has the effect of ignoring spurious excursion of the signal.

After the 18 hour point, each new 30 second slot representational value p, is first classified using hysteresis thresholding described above and the mean and standard deviation of that class is updated with conjugate prior approach (https://en.wikipedia.org/wiki/Conjugate_prior). This then updates the corresponding Threshold $T_{ON}$ or $T_{OFF}$. To protect against drift, the thresholds are optionally recomputed from scratch every 48 hours.

Figure 8:
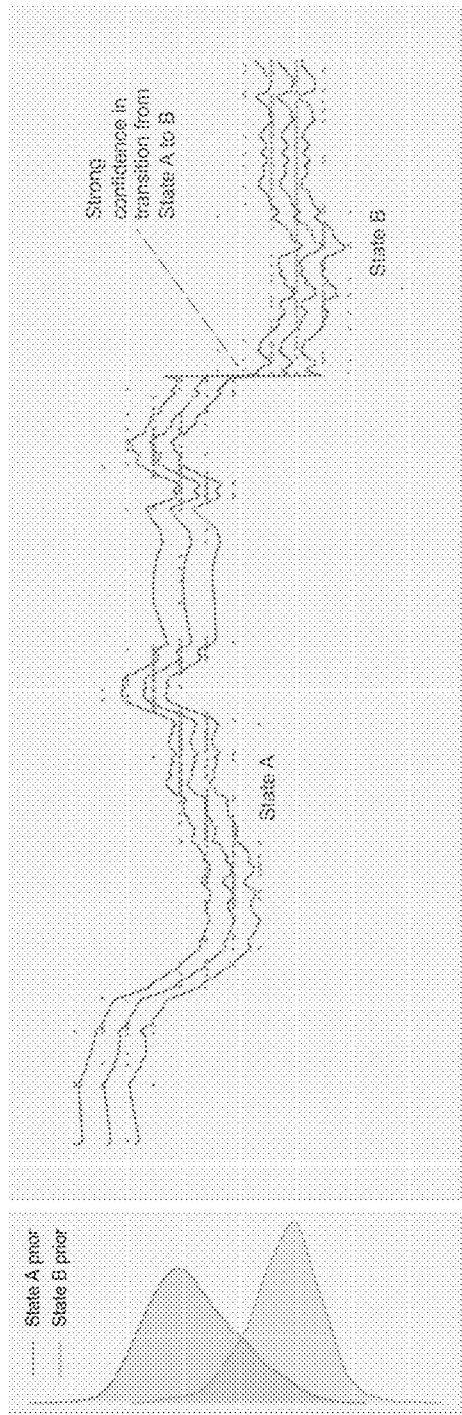
FIG. 8 is an example of a full night tracking, including identification of the addition of a second person to the bed.

In one embodiment, a supervised approach is alternately used. To remove the 18 hour wait constraint of the unsupervised approach, and to increase robustness against mechanical noise, a supervised approach may be used. In this approach a multi-layered neural network is trained on known ON/OFF labels with the following inputs:

(a) Spectrograms of Heart Rate (50,450 RPM) and Breathing Rate (6,24 RPM) sub-bands (b) Optionally, the distribution of the unsupervised approach or the computed low and high peaks or the thresholds $T_{ON}$ and $T_{OFF}$ (c) Inference over time is performed using a conditional random field model, with dependent transition probabilities FIG. 8 is an example of a full night tracking, including identification of the addition of a second person to the bed. As can be seen, there is a change in heartbeat frequency detected in one sensor channel when a second user gets on the bed, aided by longitudinally tracked data for two users.

The system shows the two state histograms on the left, showing a strong confidence in the transition from state A to state B.

Figure 9A:
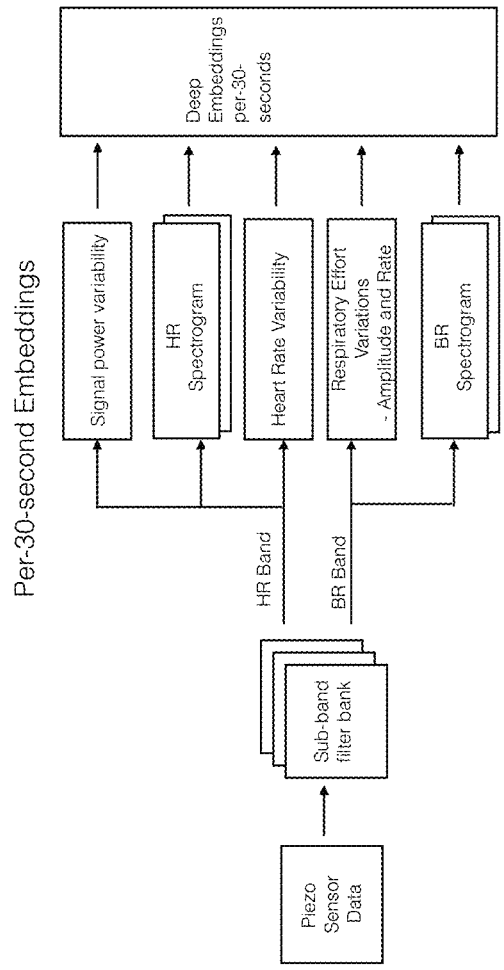
FIG. 9A is a block diagram of one embodiment of identifying sleep stages.

FIG. 9A is a block diagram of one embodiment of identifying sleep stages. Sleep stages, including awake, light sleep (also called N1 or N2), deep sleep (also called N3 or N4), and REM sleep, are typically measured using EEG and scored by a polysomnographic technologist. In one embodiment, the present system for estimates these sleep stages, based on piezo force sensor data, at each 30 second period of time using a full night of sleep. One key signal the system uses is the amplitudes and durations of the peaks and valleys (rise and fall) of the breathing force. The system is able to detect REM sleep to good accuracy.

The piezo force sensor data is processed to capture the time and amplitude of the peak and valley (rise and fall) of each breath or motion. Deep learning models using the labeled data detect the sleep staging (AWAKE, LIGHT, DEEP, REM). Sequences of deep embeddings per 30 seconds are fed into full night convolutional and recurrent deep learning models for full night predictions.

FIG. 9B illustrates the difference between REM and DEEP sleep breathing, which may be used in analyzing an identifying sleep stages.

Figure 10:
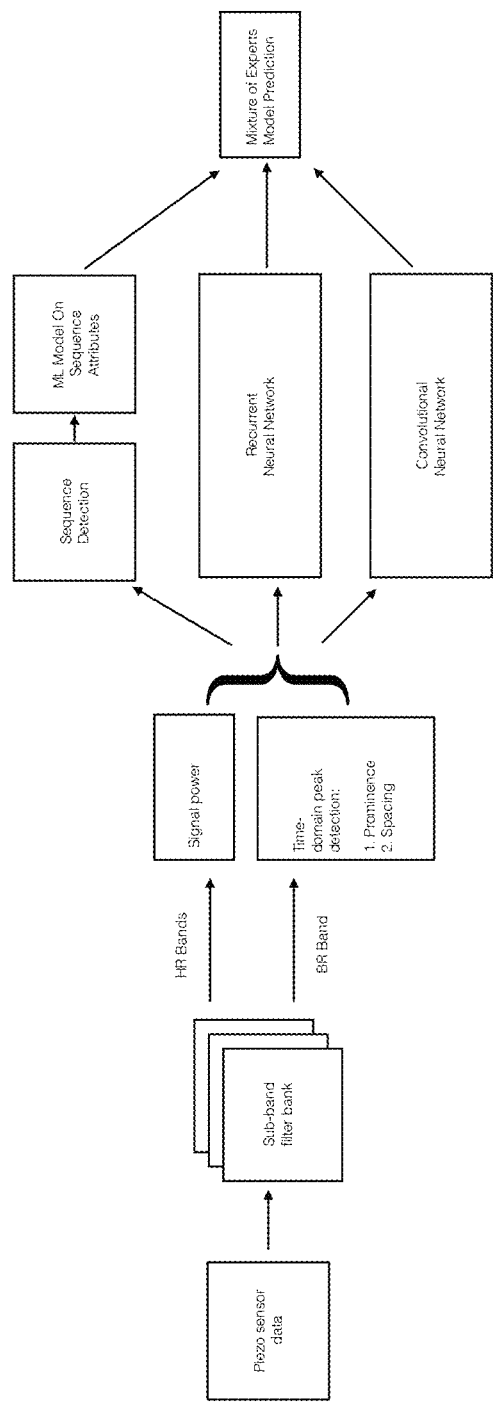
FIG. 10 is a block diagram of one embodiment detecting a respiratory event.

FIG. 10 is a block diagram of one embodiment detecting a respiratory event. Respiratory Events (including Apnea, Hypopnea, and Respiratory Event Related Arousals) are a prevalent problem. Often an individual is struggling for breath or ceases to breathe at all for a period of up to 90 seconds. These events often repeat one after another, forming a sequence of respiratory events. If coupled with oxygen desaturation (and if a greater than a threshold of such events occur in the night) this would indicate Sleep Apnea, a serious issue that has negative health consequences in the long term.

In one embodiment, the system may correlate the various data types analyzed. For example, an increase in heart rate leading and shortly after the respiratory event could indicate advanced apnea.

In one embodiment, the system may be integrated with an SPO2 device through Apple Healthkit or equivalent software, or through the use of a SPO2 finger pulse-oximeter. In one embodiment, CO2 exhalation may also be used to monitor the user's breathing, in one embodiment.

Force is transmitted through a mattress from body movement due to breathing or attempts at breathing. The piezo force sensor data is processed to capture the time and amplitude of the peaks and valleys (rise and fall) of each breath or motion. Deep learning models using the labeled data detect sequences of likely respiratory events.

Figure 11A:
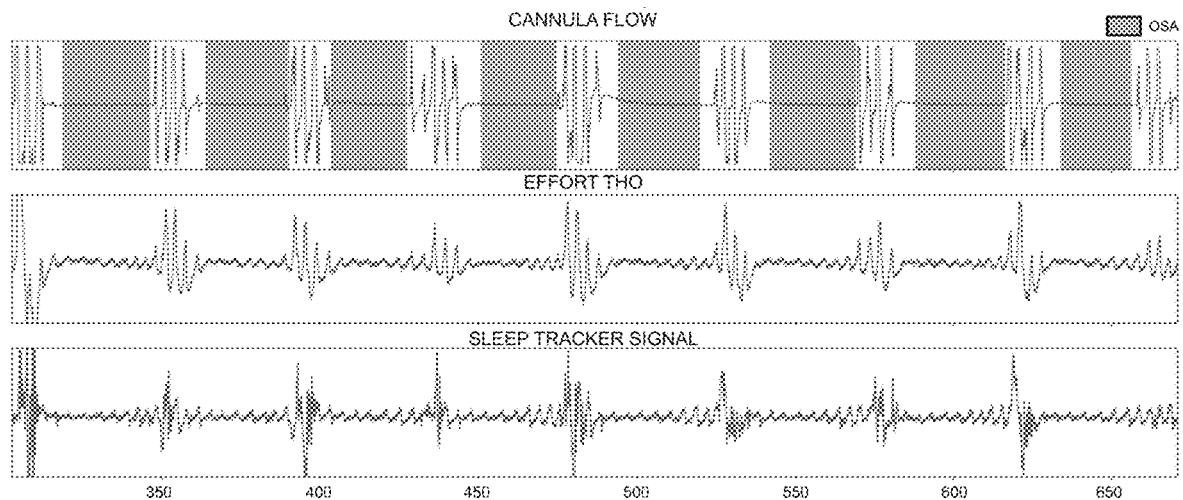
FIGS. 11A and 11B are diagrams illustrating exemplary signals which may be used in identifying a respiratory event.
Figure 11B:
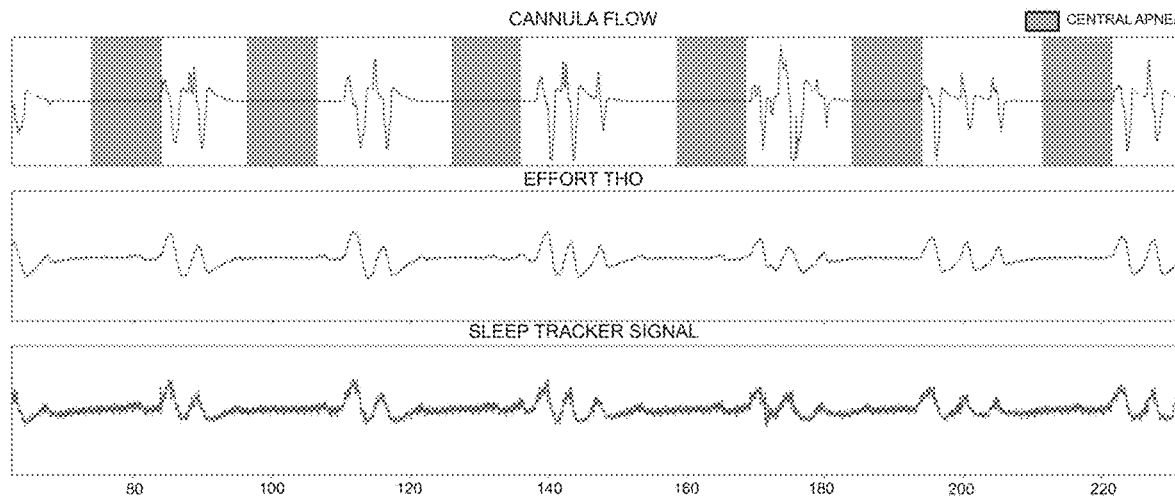

FIG. 11A is a diagram illustrating exemplary signals which may be used in identifying an obstructive apnea respiratory event. The figure shows the cannula flow data (measure of air flow through the nostrils), effort THO is a chest-movement based measurement, and the data from the sensors of the present application. As can be seen, the sensor data closely represents the breathing pattern shown by the cannula flow data. The respiratory events show alternation of diminished breathing amplitude and breakthrough events exhibiting large breathing amplitude are characteristics of respiratory events. In contrast, healthy breathing is generally even in depth over time, through a particular sleep phase. FIG. 11B is a diagram illustrating exemplary signals which may be used in identifying central apnea respiratory events.

Currently, sleep apnea is typically diagnosed by sending someone to a PSG sleep lab for a single night. As part of the PSG sleep analysis, the density of apnea events is calculated (the number of them per hour of sleep) and then a designation of no apnea, mild apnea, etc. is concluded based on the data from that single night. In contrast, the present system can monitor these events non-invasively for many nights in the user's home environment and get a much better reading of the density of these apnea events "typically" occurring as opposed to a single reading in the unnatural sleep lab.

Figure 12A:
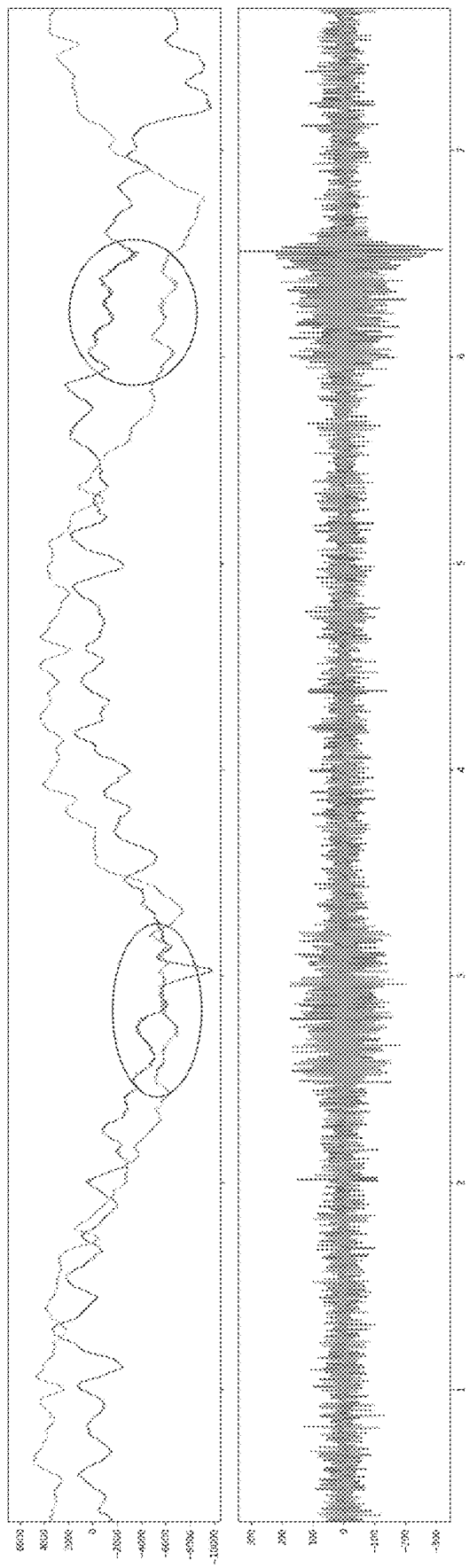
FIGS. 12A and 12B are diagrams illustrating exemplary signals which may be used in identifying snoring and associating it with a particular user.

FIG. 12A is a diagram illustrating exemplary signals which may be used in identifying snoring and associating it with a particular user.

Because of the sensitivity of the piezo sensors and the preservation of detailed signal data, the present application detected subtle vibrations at 30-120 Hz in our (piezo) force sensor signal. This was caused by subtle mechanical vibrations caused by snoring and related airway-disturbances vibrating the body and then traveling through the mattress to the (piezo) force sensor. This transmission is not audio or pressure or pressure-wave based, but rather is based on mechanical forces from high-frequency vibrations of the body traveling through the mattress. This unique method of identifying snoring provides useful and accurate data.

In one embodiment, the system processes these small amplitude 30-120 Hz vibrations together with breath detection for up to two users on the bed to validate and attribute any detected snoring to the correct user (this includes the possibility of detecting snoring from both users simultaneously).

In one embodiment, a system, trained using labeled data, and combining two deep learning models is used:

The first detects likely snoring-based vibrations.

The second validates and attributes the snoring-based vibrations to a user given a breathing signal.

Because the snoring is associated with the a particular part of the breathing in, by analyzing the vibration in light of the breathing signal, the system can attribute the snoring to the correct user. This would not be possible using conventional microphone based measurements.

Figure 12B:
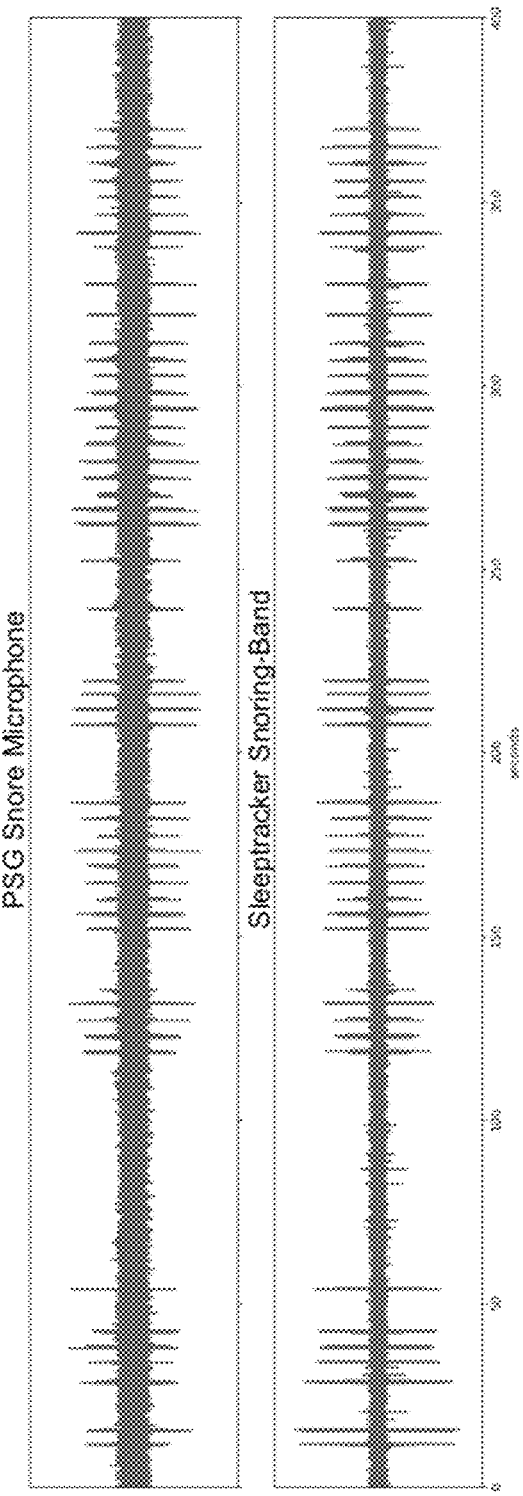

FIG. 12A illustrates the piezo force sensor data showing the full signal and the isolated snoring vibrations. As can be seen, the signal data is not cleanly additive, therefore the trained deep learning system is used to identify and isolate the snoring vibrations for analysis. FIG. 12B illustrates an example of looking at the snoring band of the data collected by the present system and comparing that to the PSG equipment's microphone which is detecting the snoring. It is clear visually that there is excellent correlation. The piezoelectric sensor is able to pick up high frequency signals including the vibrations associated with snoring.

Figure 13:
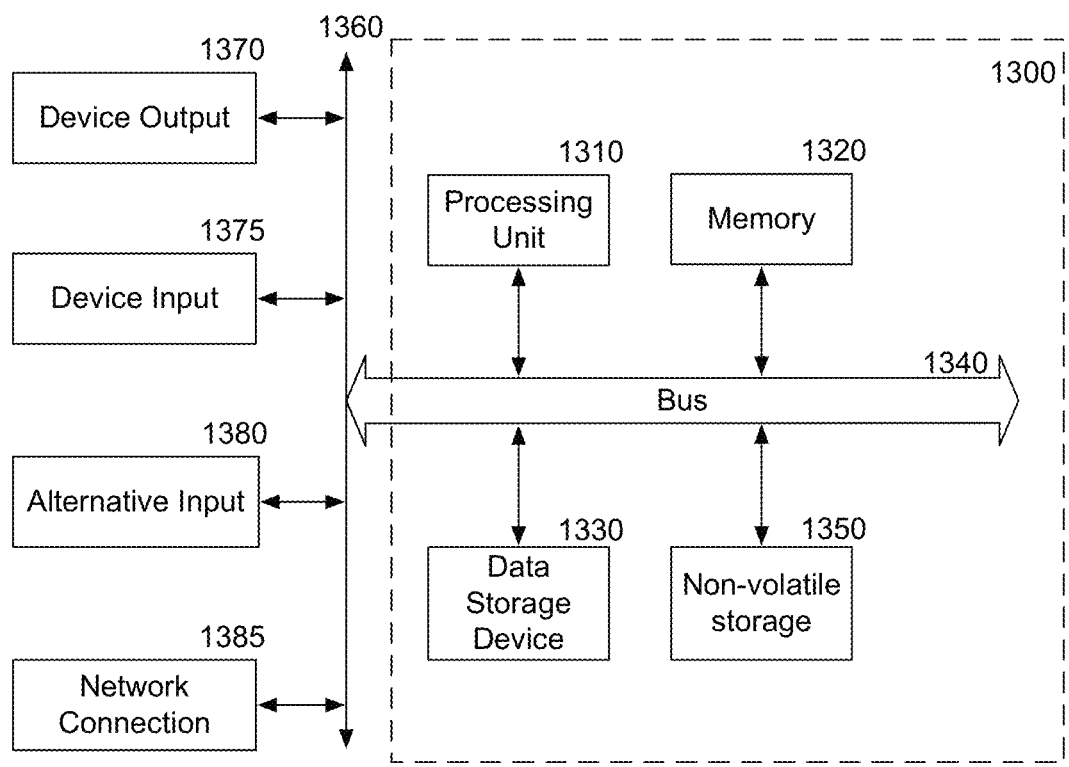
FIG. 13 is a block diagram of a computer system which may be used with the present invention.

FIG. 13 is a block diagram of one embodiment of a computer system that may be used with the present invention. It will be apparent to those of ordinary skill in the art, however that other alternative systems of various system architectures may also be used. Furthermore, while this is a particular computer system, the processors, servers, and other computer devices described may be implemented in a distributed cloud-based environment in which portions of a computer system's capabilities are used to provide the described features and processes.

The data processing system illustrated in FIG. 13 includes a bus or other internal communication means 1340 for communicating information, and a processing unit 1310 coupled to the bus 1340 for processing information. The processing unit 1310 may be a central processing unit (CPU), a digital signal processor (DSP), or another type of processing unit 1310.

The system further includes, in one embodiment, a random access memory (RAM) or other volatile storage device 1320 (referred to as memory), coupled to bus 1340 for storing information and instructions to be executed by processor 1310. Main memory 1320 may also be used for storing temporary variables or other intermediate information during execution of instructions by processing unit 1310.

The system also comprises in one embodiment a read only memory (ROM) 1350 and/or static storage device 1350 coupled to bus 1340 for storing static information and instructions for processor 1310. In one embodiment, the system also includes a data storage device 1330 such as a magnetic disk or optical disk and its corresponding disk drive, or Flash memory or other storage which is capable of storing data when no power is supplied to the system. Data storage device 1330 in one embodiment is coupled to bus 1340 for storing information and instructions.

The system may further be coupled to an output device 1370, such as a cathode ray tube (CRT) or a liquid crystal display (LCD) coupled to bus 1340 through bus 1360 for outputting information. The output device 1370 may be a visual output device, an audio output device, and/or tactile output device (e.g. vibrations, etc.)

An input device 1375 may be coupled to the bus 1360. The input device 1375 may be an alphanumeric input device, such as a keyboard including alphanumeric and other keys, for enabling a user to communicate information and command selections to processing unit 1310. An additional user input device 1380 may further be included. One such user input device 1380 is cursor control device 1380, such as a mouse, a trackball, stylus, cursor direction keys, or touch screen, may be coupled to bus 1340 through bus 1360 for communicating direction information and command selections to processing unit 1310, and for controlling movement on display device 1370.

Another device, which may optionally be coupled to computer system 1300, is a network device 1385 for accessing other nodes of a distributed system via a network. The communication device 1385 may include any of a number of commercially available networking peripheral devices such as those used for coupling to an Ethernet, token ring, Internet, or wide area network, personal area network, wireless network or other method of accessing other devices. The communication device 1385 may further be a null-modem connection, or any other mechanism that provides connectivity between the computer system 1300 and the outside world.

Note that any or all of the components of this system illustrated in FIG. 13 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 1320, mass storage device 1330, or other storage medium locally or remotely accessible to processor 1310.

It will be apparent to those of ordinary skill in the art that the system, method, and process described herein can be implemented as software stored in main memory 1320 or read only memory 1350 and executed by processor 1310. This control logic or software may also be resident on an article of manufacture comprising a computer readable medium having computer readable program code embodied therein and being readable by the mass storage device 1330 and for causing the processor 1310 to operate in accordance with the methods and teachings herein.

The present invention may also be embodied in a handheld or portable device containing a subset of the computer hardware components described above. For example, the handheld device may be configured to contain only the bus 1340, the processor 1310, and memory 1350 and/or 1320.

The handheld device may be configured to include a set of buttons or input signaling components with which a user may select from a set of available options. These could be considered input device #1 1375 or input device #2 1380. The handheld device may also be configured to include an output device 1370 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 1310, a data storage device 1330, a bus 1340, and memory 1320, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 1385.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1310. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A method of detecting the presence of a user on a bed comprising:
receiving movement data associated with the user on the bed in pseudo-real-time;
collecting the received movement data over a plurality of time periods;
extracting features from the movement data for at least one of the plurality of time periods in pseudo-real-time;

determining whether the bed is occupied for the plurality of time periods in pseudo-real-time based on the extracted features;

for a subset of the plurality of time periods in which the bed is determined to be occupied, identifying a user on a first side of the bed, based on the extracted features;

recording the user's on-bed and off-bed time segments;

determining a sleep schedule associated with the user based on the user's on-bed and off-bed time segments;

utilizing a sleep engine to determine sleep stages for the user based on the extracted features and the sleep schedule;

adjusting the bed when at least one of a respiration event and snoring is detected, the detecting based on the extracted features from the movement data;

determining when the extracted features of a majority of the at least one of the plurality of time periods indicates that the sleep stage for the user is awake; and providing a sleep recording to the user, showing the sleep stages for the user.

2. The method of claim 1, further comprising:
measuring the movement data using a piezo force sensor.

3. The method of claim 1, wherein the movement data comprises micromovements of the bed and wherein:
determining whether the bed is occupied is based at least on the extracted features associated with the micromovements of the bed and mapping the micromovements of the bed to human movements.

4. The method of claim 1, further comprising:
pruning sections of the sleep recording where the user has less than one sleep episode.

5. The method of claim 1, further comprising:
when there is a plurality of users, identifying a snoring user of the plurality of users, based on vibrations in the movement data, and attributing the snoring to the snoring user, the determining based solely on the extracted features.

6. A sleep detection system comprising:
a receiver coupled to sensors on a bed to receive movement data from the sensors on the bed in pseudo-real-time;

a memory for storing the received movement data covering a plurality of time periods;

a deep-learning system executed by a processor to extract features from the movement data for at least one of the plurality of time periods in pseudo-real-time to determine whether the bed is occupied for the plurality of time periods in pseudo-real-time based on the extracted features;

an identifier executed by the processor, for a subset of the time periods in which the bed is determined to be occupied, to determine an identity of a user on a first side of the bed, based on the extracted features;

a sleep engine executed by the processor to determine sleep stages for the user based on the extracted features;

a controller to adjust the bed when at least one of a respiration event and snoring is detected, the adjusting based on the extracted features;

a recording system to record in the memory the user's on-bed and off-bed time segments, wherein the deep-learning system is configured to determine a sleep schedule associated with the user based on the user's on-bed and off-bed time segments;

multi-layered neural network executed by the processor to determine when a majority of the determined sleep stages indicate that the sleep stage for the user is awake; and a sleep recording stored in a memory to show the sleep stages for the user.

7. The sleep detection system of claim 6, further comprising:
a piezo force sensor to measure the movement data.

8. The sleep detection system of claim 6, wherein the movement data comprises micromovements of the bed and wherein the deep-learning system determines whether the bed is occupied based at least on the extracted features associated with the micromovements of the bed and mapping the micromovements of the bed to human micromovements.

9. The sleep detection system of claim 6, wherein the sleep recording is pruned of sections, by the processor, where the user has less than one sleep episode.

10. The sleep detection system of claim 6, wherein the deep-learning system identifies a snoring user of a plurality of users, based on vibrations in the movement data, and attributes the snoring to the snoring user, the identifying based solely on the extracted features.

11. A system to analyze sleep comprising:
a plurality of sensors to collect movement data of a user on a bed in pseudo-real-time, the movement data collected over a plurality of time periods;

a sensor-fusion deep-learning system executed by a processor to extract features from the movement data for at least one of the plurality of time periods in pseudo-real-time and to determine whether the bed is occupied for the plurality of time periods in pseudo-real-time based on the extracted features;

a tracking system executed by the processor to track the movement data, for each time period in which the bed is determined to be occupied based on the extracted features;

an attribution system executed by the processor to attribute the movement data to an identified user identified based on the extracted features on a first side of the bed, based on the extracted features;

a sleep engine executed by the processor to determine sleep stages for the user, based on the extracted features;

a controller to adjust the bed when at least one of a respiration event and snoring is detected, the adjusting based on the extracted features;

a recording system to record in a memory the user's on-bed and off-bed time segments, wherein the sensor-fusion deep-learning system is configured to determine a sleep schedule associated with the user based on the user's on-bed and off-bed time segments, based on the extracted features;

a multi-layered neural network executed by the processor to determine when a majority of the determined sleep stages indicate that the sleep stage for the user is awake; and an output device to provide the user with a sleep recording showing the sleep stages for the user.

12. The system of claim 11, wherein the plurality of sensors includes a piezo force sensor.

13. The system of claim 11, wherein the tracking system tracks micromovements of the bed and maps the micromovements of the bed to human micromovements, to determine whether the bed is occupied.

14. The system of claim 11, wherein the sleep recording is pruned of sections, by the processor, where the user has less than one sleep episode.

* * * * *